(12) United States Patent
Shi et al.

(10) Patent No.: US 8,282,970 B2
(45) Date of Patent: Oct. 9, 2012

(54) THEAFLAVIN COMPOSITIONS, RELATED PROCESSES AND METHODS OF USE

(75) Inventors: Xiaowei Shi, Edison, NJ (US); Xueyin Ren, Wuxi (CN); Jianhong Liu, Wuxi (CN); Houjian Cao, Changzhou (CN); Wenhao Ren, Wuxi (CN); Yizhou Cao, Jiangyin (CN)

(73) Assignee: Jiahgsu Dehe Bio-Tech Co., Ltd, Jinngsu (CN)

( * ) Notice: Subject to any disclaimer, the term of this patent is extended or adjusted under 35 U.S.C. 154(b) by 103 days.

(21) Appl. No.: 12/574,862

(22) Filed: Oct. 7, 2009

(65) Prior Publication Data
US 2011/0082196 A1 Apr. 7, 2011

(51) Int. Cl.
*A61K 36/82* (2006.01)

(52) U.S. Cl. .................................. 424/729; 424/774

(58) Field of Classification Search .................. None
See application file for complete search history.

(56) References Cited

U.S. PATENT DOCUMENTS

| | | | |
|---|---|---|---|
| 3,228,789 A | 1/1966 | Glassman et al. | |
| 3,845,770 A | 11/1974 | Theeuwes et al. | |
| 3,916,899 A | 11/1975 | Theeuwes et al. | |
| 4,613,672 A * | 9/1986 | Hara .............. | 549/399 |
| 4,708,834 A | 11/1987 | Cohen et al. | |
| 4,935,243 A | 6/1990 | Borkan et al. | |
| 5,698,155 A | 12/1997 | Grosswald et al. | |
| 6,113,965 A | 9/2000 | Goodsall et al. | |
| 6,143,335 A | 11/2000 | McKenzie | |
| 6,833,144 B2 | 12/2004 | Goodsall et al. | |
| 7,157,493 B2 | 1/2007 | Zhao et al. | |
| 7,247,336 B1 | 7/2007 | Fitzjarrell et al. | |
| 7,288,680 B2 | 10/2007 | Ho et al. | |
| 7,427,622 B2 | 9/2008 | Zhao et al. | |
| 2008/0131558 A1 * | 6/2008 | Hodges et al. ........... | 426/49 |

FOREIGN PATENT DOCUMENTS

| | | |
|---|---|---|
| CN | 1729807 A | 2/2006 |
| CN | 101285081 A | 10/2008 |

OTHER PUBLICATIONS

Maron et al., "Cholesterol-Lowering Effect of a Theaflavin-Enriched Green Tea Extract", Arch. Intern. Med, vol. 163, pp. 1448-1453, 2003.
Alderman, "A Review of Cellulose Ethers in Hydrophilic Matrices for Oral Controlled-Release Dosage Forms", Int. J. Pharm. Tech. & Prod. Mfr, vol. 5, No. 3, pp. 1-9, 1984.
Bamba et al., "Release Mechanisms in Gelforming Sustained Release Preparations", Int. J. Pharm, vol. 2, pp. 307-315, 1979.
Verma et al., "Osmotically Controlled Oral Drug Delivery", Drug Dev. Ind. Pharm, vol. 26, No. 7, pp. 695-708, 2000.
Manna et al., "Tea Polyphenols Can Restrict Benzo[A]Pyrene-Induced Lung Carcinogenesis by Altered Expression of P53-Associated Genes and H-RAS, C-MYC and CYCLIN D1", J. Nutr. Biochem, vol. 20, pp. 337-349, 2009.
Bhagwat et al., "Flavonoid Composition of Tea: Comparison of Black and Green Teas", 2003 IFT Annual Meeting—Chicago, poster 45I-9, Jul. 14, 2003.
Leung et al., "Theaflavins in Black Tea and Catechins in Green Tea Are Equally Effective Antioxidants", J. Nutr., vol. 131, pp. 2248-2251, 2001.
Wang et al., "Research Progress on Property and Application of Theaflavins", Afr. J. Biotechnol, vol. 5, No. 3, pp. 213-218, 2006.
Lin et al., "Theaflavins Attenuate Hepatic Lipid Accumulation Through Activating AMPK in Human HEPG2 Cells", J. Lipid Res, vol. 48, pp. 2334-2343, 2007.
Xie et al., "Antioxidant Properties of Fractions and Polyphenol Constituents From Green, Oolong and Black Teas", Proc. Natl. Sci. Counc. Repub. China B, vol. 17, No. 2, pp. 77-84, 1993.
Lin et al., "New Phenolic Components and Chromatographic Profiles of Green and Fermented Teas", J. Agricult. Food Chem, vol. 56, pp. 8130-8140, 2008.
Graham, "Green Tea Composition, Consumption, and Polyphenol Chemistry", Pre. Med, vol. 21, pp. 334-350, 1992.

* cited by examiner

*Primary Examiner* — Susan Hoffman
(74) *Attorney, Agent, or Firm* — Jules E. Goldberg (57) ABSTRACT

A process for producing purified theaflavin extract is provided which comprises combining an organic solvent with tea leaves, extracting polyphenols from the tea leaves to produce an organic stock substrate solution; producing a second batch of tea leaves; grinding the second batch of tea leaves to produce stock fermentation enzyme; combining the stock substrate solution with the stock fermentation enzyme to produce a fermentation mixture; fermentation of the mixture to produce theaflavins; and, separating the theaflavins from the fermentation mixture to produce purified theaflavin extract. Oral dosage forms are provided which comprise an effective amount of the purified theaflavin extract. Methods of treatment of human physiological disorders are provided which comprise administering an oral dosage form.

17 Claims, 1 Drawing Sheet

THEAFLAVIN COMPOSITIONS, RELATED PROCESSES AND METHODS OF USE

FIELD OF THE INVENTION

The present invention relates to processes for production of purified theaflavin extract, compositions which result from the processes, oral dosage forms, and methods of use.

BACKGROUND OF THE INVENTION

Theaflavin (catechin dimer joined at B rings) and its derivatives, known collectively as theaflavins, are antioxidant polyphenols Flavan-3-ols formed from catechins during enzymatic oxidation (fermentation). Theaflavins generally comprise a mixture of theaflavin, theaflavin-3-gallate, theaflavin-3'-gallate and theaflavin-3,3'-digallate.

Theaflavins have positive health benefits directly linked to the antioxidant properties of these compounds. The benefits include the ability to effect lower blood lipid levels (e.g. cholesterol), control of inflammation, as well as anti-tumor effects. See, e.g., Maron D J, et al., *Cholesterol-Lowering Effect of a Theaflavin-Enriched Green Tea Extract: a Randomized Controlled Trial*, Arch. Intern. Med. 163 (12): 1448 (2003). See, also, Lorentz, M., et al., Basic Res Cardiol. 2009 January; 104(1):100; Manna, S., et al., J Nutr Biochem. 2009 May; 20(5):337.

Limited availability of theaflavins, economically derived from natural sources, however, presents a significant barrier to realization of the health benefits of theaflavins. Commercial reagents such as polyphenol peroxidase and hydrogen peroxide from commercial sources are often used in the fermentation step, which further increases the cost of the production. Goodsall, et al., U.S. Pat. Nos. 6,833,144; 6,113,965. Many current extraction and purification steps employ environmentally unfriendly solvents methanol and chloroform. Environmental hazards moreover result from current processes due to the frequent application of strong acids and bases and large amounts of resulting waste generated.

An ongoing need for low cost, high yield, environmentally friendly scalable production of theaflavins from natural sources indeed exists toward realization of numerous health benefits.

SUMMARY OF THE INVENTION

A process for producing purified theaflavin extract is provided which comprises combining an organic solvent with tea leaves, extracting polyphenols from the tea leaves to produce an organic stock substrate solution; producing a second batch of tea leaves; grinding the second batch of tea leaves to produce stock fermentation enzyme; combining the stock substrate solution with the stock fermentation enzyme to produce a fermentation mixture; fermentation of the mixture to produce theaflavins; and, separating the theaflavins from the fermentation mixture to produce purified theaflavin extract.

In addition, the current invention is directed to Oral dosage forms which comprise an effective amount of the purified theaflavin extract.

The invention is further directed to methods of treatment of human physiological disorders are provided which comprise administering an oral dosage form.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference including U.S. Pat. Nos. 7,427,622; 7,157,493 and 7,288,680.

As used herein the term organic solvent refers to any inert organic solvent that solubilizes tea leaf polyphenols including but not limited to esters, alcohols, ketones and ethers. The term inert as used herein refers to an organic solvent that does not otherwise affect the oxidation of polyphenols to theaflavins in the processes described herein. Esters for use as organic solvent in processes described herein include, but are not limited to, for example, methyl acetate, ethyl acetate, propyl acetate, and isopropyl acetate. Alcohols for use as organic solvent in processes described herein include, but are not limited to, for example, ethyl alcohol, propyl alcohol, and isopropyl alcohol. Ketones for use as organic solvent in processes described herein include, but are not limited to, for example, acetone and butanone. Ethers for use as organic solvent in processes described herein include, but are not limited to, for example, diethyl ether, dipropyl ether, and methyl-tert-butyl ether.

The term organic stock substrate solution, as used herein, refers to an organic tea leaf extract containing polyphenols.

The term stock fermentation enzyme, as used herein, refers to a source of endogenous enzymes in tea leaves, polyphenol oxidase (PO) and polyphenol peroxidase (PPO) for example.

The term fermentation mixture, as used herein, refers to an organic tea leaf extract containing polyphenols mixed with endogenous enzymes in tea leaves and wherein the polyphenols undergo oxidation to flavins by means of the enzymes including polyphenol oxidase (PO) and polyphenol peroxidase (PPO).

The term water, as used herein has its ordinary meaning, but includes acidic aqueous and basic aqueous.

The term human physiological disorder as used herein refers to inflammation and related disease, including but not limited to, hyperlipidemia, coronary heart disease, apoplexy, arthesclerotic cardiovascular diseases, AIDS, diabetes, oxidated-low density lipoprotein level, von Willebrand's disease, leukopenia, cerebral infarction, dementia and physical disorder, and fatty liver.

The term oral dosage form as used herein includes but is not limited to a tablet, capsule, powder, solution, suspension, emulsion, pill, pellet, sustained-release formulation that contain an effective amount of theaflavins produced by methods according to the present invention. However, since theaflavins produced by methods according to the present invention are incorporated into food items such as nutritional bars and nutritional drinks the term oral dosage form includes food and drink items that incorporate an effective amount of theaflavins produced by methods according to the present invention.

As used herein the term theaflavins includes but is not limited to theaflavin, isotheaflavin, neotheaflavin, theaflavin-3-gallate, theaflavin-3'-gallate, theaflavin-3,3'-digallate, epitheaflavic acid, epitheaflavic acid-3'-gallate, theaflavic acid, theaflavic acid-3'-gallate and mixtures thereof. The term includes salt forms of these compounds.

Fermentation refers to an oxidative process to produce theaflavins, and optionally thearubigins.

Fermentation enzyme refers to the native reagents of tea leaves which effect fermentation. Preferably whole tea leaves optionally treated with a solvent, preferably moisturized with aqueous solution, pure water or 0.05%-1% of citric acid solution, for example, frozen, and then ground, preferably to particles, for example, smaller than about 100 mesh.

The term "washing" refers to a process of mixing thoroughly an organic phase with an aqueous phase, separating the organic phase from the aqueous phase, and collecting the organic phase. Optionally, this process can be repeated one or more times and the organic phases are combined.

Solute transferring refers to a process of adding an aqueous phase to an organic phase to form a mixture, concentrating said mixture and forcing the solute in the organic phase to be transferred into the aqueous phase.

This present invention provides an improved process for economic manufacture of high quality theaflavins wherein tea polyphenols are extracted into an organic solvent and oxidized, for example, in the organic solvent by means of native enzymes directly from tea leaf material without using other source of polyphenols. The fermentation process takes place in an organic phase, which not only improves the yield of theaflavins at low cost, but avoids problems such as emulsions in other manufacturing processes in multiphase media. Process embodiments of the present invention employ, for example, neutral or weakly acidic conditions.

An improved process for manufacturing theaflavins is described comprising the steps of extracting preferably green tea leaves with an organic solvent to produce an organic stock substrate solution, preparing stock fermentation enzyme from tea leaves, and fermenting the organic stock substrate solution with the stock fermentation enzyme, for example, in an oxygenated environment to produce a fermentation mixture. Embodiments of the process described herein include filtering the resulting fermentation mixture and concentrating the resulting filtrate. Embodiments include washing the filtrate with an aqueous solution, then adding water to the washed filtrate and concentrating the resulting aqueous phase to produce aqueous theaflavin extract by removing, evaporating for example, remaining organic solvent. Embodiments include filtration of the aqueous theaflavin extract to remove insoluble impurities at this point to produce purified aqueous theaflavin extract. Embodiments include lyophilization or spray drying of the purified aqueous theaflavin extract to produce solid purified theaflavin extract. Example solid purified theaflavin extract compositions produce by the processes described herein contain about 45% theaflavins. Treatment of human physiological disorders are provided which comprise administering an effective amount of purified theaflavin extracts described herein. Oral dosage forms are provided which comprise an effective amount of purified theaflavin extracts described herein.

Example Theaflavin Extract Characteristics Resulting from Novel Processes:

TABLE I

| characteristics | Appearance and result | Note |
| --- | --- | --- |
| | Pale yellow to red brown color, astringent | |
| theaflavin content % | ≧40.0 | HPLC analysis method |
| Water content % | ≦6.0 | |
| Ash content % | ≦2.0 | |
| Heavy metal (ppm) | ≦10 | |
| arsenic (ppm) | ≦2 | |
| caffeine % | ≦4 | |

The present invention has a number of advantages over traditional processes. Because the fermentation process takes place in an organic phase and tea leaves, homogenized for example, are used as the source of fermentation enzyme, the manufacturing process is readily controllable and avoids problems such as emulsifications in traditional processes. In addition, this low cost manufacturing process produces theaflavins in high quality with a theaflavin content of up to 45% by weight determined by HPLC. The caffeine level, for example, is reduced to about 4% or less. The solubility, taste, and color of the product are significantly improved. Processes described herein, without using toxic solvent or generating large amount of waste, are environmentally friendly. Organic solvent is recycled, for example. Neutral or weakly acidic aqueous conditions are employed, for example, to enhance the quality of the product.

An exemplary embodiment process of the present invention includes but is not limited to, for example:

a. Preparation of fermentation stock solution (extracting of green leaves with an organic solvent): 500 Kg, for example, Green tea leaves are added into an extractor (Multifunctional Dynamic Extracting Tank; Model: ZY-DTQ-6.0; Manufacturer: Wenzhou Zhongyuan Light Industry Machine Co., for example), followed by the addition of 5000 Kg, for example, ethyl acetate. The mixture is stirred and extracted for 10-120 minutes, for example, at 10° C.-90° C., for example. The organic phase is collected. A second portion of 5000 Kg, for example, ethyl acetate is used for extracting the green tea leaves. The organic phases are combined, and concentrated at 0.06 Mpa, for example, at below 80° C., for example, (Scraped Evaporator, Model: ZYE-40; Manufacturer: Changshu Pharmaceutical & Chemical Equipment General Factory, for example) until a solid content of between about 0.5% and about 5% is reached; then cooled to room temperature and used as the fermentation stock solution.

b. Preparation of fermentation enzyme: Fresh tea leaves 600 Kg, for example, are moisturized using pure water or 0.01%-1%, for example, of citric acid solution, frozen, and ground (40-100 Mesh, for example) as the fermentation enzyme.

c. Fermentation: 5000 L, for example, of fermentation stock solution obtained from step (a) is added to a fermentor (Model: FXG; Manufacturer: Changshu Pharmaceutical & Chemical Equipment General Factory, for example), followed by the addition of 500 Kg, for example, fermentation enzyme from step (b). The mixture in the fermentor undergoes fermentation process in the presence of gas, e.g., air with an agitation at 20° C.-60° C., for example. The air flow rate is controlled at range of, for example, 0.2-40 m$^3$/min, agitation speed, for example, 30-150 rpm. The ratio of fermentation stock solution and the enzyme by weight, for example, is between about 5:1 to about 40:1.

d. Separation: The fermentation solution from the step (c) is filtered through, for example, 120 mesh filter screen and divided into filtrate and filter residue.

e. Concentration: The filtrate from the step (d) is concentrated, for example, using Scraped Evaporator under conditions, for example, of relative vacuum 0.06 Mpa and temperature preferably below 80° C. (Model: ZYE-40; Manufacturer: Changshu Pharmaceutical & Chemical Equipment General Factory, for example) to solid content, for example, of 5%-30%.

f. Washing: The concentrated filtrate from the step (e) is put into water scrubber (Washing Vessel, Model: SX1000, Manufacturer: Changshu Pharmaceutical & Chemical Equipment General Factory, for example) and then the acidic solution is added. The mixture is stirred up and then allowed to stand to separate into two layers. The bottom aqueous layer is removed. The remaining organic phase is washed 1-20 times using the same method as above. The ratio of the acidic solution and concentrate by volume is about 0.1:1-20:1, for example. After washing, the organic phase and aqueous phase are collected, respectively. The aqueous phase is concentrated and dried to form the by-product. The organic phase is used in the next step.

g. Solute transferring: Pure water is added into the organic phase solution obtained from the above step (f). The ratio of pure water and organic phase solution is bout 1:1-1:50 by weight, for example. The organic phase and water are mixed thoroughly and concentrated at controlled temperature.

h. Filtration: The concentrate obtained from step (g) is cooled to 10° C.-60° C., for example, and filtered. The filtrate is collected.

i. Concentrating and freeze-drying: The filtrate obtained from the step (h) is further concentrated to solid content of 15%-80%, for example, by using High Efficiency Rotary Scraped Evaporator (Model: DN1200; Manufacturer: Wuxi Xuelang Fermentation Equipment Co., Ltd.) at relative vacuum 0.085 Mpa, for example, and temperature below 80° C., for example. The concentrate is subjected to spray drying, or lyophilization, then ground using high speed mill, for example, and screened using screen grader, for example, to obtain the product of theaflavins.

Exemplary modifications of processes of the present invention, exemplified a-i, supra, include embodiments wherein the ratio of tea leaves, preferably green tea, and ethyl acetate each time in step (a) above for the preparation of fermentation stock solution is within the range of about 1:10 to about 1:30. The example process of preparation of enzyme in step (b) is performed at below 0° C., for example, between about −10° C. and 0° C., for at least about 2 hours. The size of ground fresh tea leaves is preferably about 80 mesh or smaller. Gas introduced into the fermentation process in step (c) is preferably pure oxygen. The temperatures in the concentration (step (e)) and transferring solute (step (g)) are controlled at below 80° C., for example between about 60° C. and about 80° C.]. The acidic solution added in washing process in step (f) is about 0.05% to about 1% of aqueous citric acid. The temperatures of the lyophilization process for concentration in step (i) are preferably controlled at below about −35° C. to form an ice block. The vacuum level is preferably about 0.6-1 mmHg while water vapor is evaporated from the ice block. The temperature is then increased, for example, at a rate of 1-5° C./hour to 0° C., then, for example, at a rate of 1-10° C. to 25° C.-30° C. and stayed, for example, for 1-4 hours until the water content of the product reaches about 3% to about 5%, for example. The vacuum is removed to obtain, for example, a theaflavins product of the present invention.

Preferred embodiment processes of the present invention are wherein the controlled temperature is between 25-60° C., for example, for extracting green tea leaves. A further example is wherein the fermentation stock solution and said fermentation enzyme are in a ratio of about 5:1 to about 20:1 by weight. Another example process feature is wherein said second controlled temperature is between 20-40° C. Solid product may be obtained by means of spray drying or lyophilization, for example.

Preparation of fermentation stock solution (organic stock substrate solution) for fermentation enzymatic oxidation:

To a container, green tea leaves, preferably shredded into 5-60 mesh, are added, followed by the addition of ethyl acetate. The ratio of green tea leaves and ethyl acetate added is between about 1:5 and about 1:30 by weight, for example. The mixture is stirred and extracted for 10-120 minutes, for example, at 10° C.-90° C., for example. The extracted solution is collected by filtration or decantation. To the resulting solid residue ethyl acetate is added. The ratio of solid residue and ethyl acetate at this point is between about 1:5 and about 1:30 by weight, for example. The extraction procedure is repeated to yield a second extraction. Extracted ethyl acetate solutions, for example, are combined to one container, concentrated at vacuum 0.085-0.054 Mpa at 56-80° C. in a rotating evaporator (e.g., model: RE-200, Shanghai Kexing Instrument Co.) to solid content in the range of 0.5%-5%, and cooled to room temperature as the fermentation stock solution (organic stock substrate solution).

Preparation of fermentation Enzyme (stock fermentation enzyme), e.g., polyphenol oxidase and polyphenol peroxidase: Fresh tea leaves are moistened with pure water or 0.01%-1% of citric acid aqueous solution, for example, frozen for at least about 2 hours, for example, then ground and filtered through a screen, preferably of at least about 80 mesh, resulting in an example stock fermentation enzyme.

Fermentation process: The fermentation stock solution (organic stock substrate solution) is added to a fermentor (fermentation container), followed by the addition of the fermentation enzyme (stock fermentation enzyme). A preferred ratio of fermentation stock solution and the enzyme is between about 5:1 and about 40:1 by weight. Gas, preferably pure oxygen, is introduced into the resulting mixture in the fermentor while stirred at about 30- to about 150 rpm, for example. The fermentation (enzymatic oxidation) is preferred to proceed at about 20° C. to about 60° C.

Separation: The fermentation solution mixture is separated (theaflavins from the fermentation mixture to produce purified theaflavin extract) by filtration, for example, and divided into filtrate and solid residue.

Concentration: The filtrate (theaflavin extract) is concentrated on a rotating evaporator (e.g. rotating evaporator (Model: RE-200, Manufacturer: Shanghai Kexing Instrument Co.) at controlled temperature to yield a mixture with about 5% to about 30% solid content.

Washing: Concentrated mixture is transferred to a water scrubber (e.g., Pear Shaped Separatory Funnel, 500 ml, Manufacturer: Shanghai Shendi Glassware Co.) followed by acidic solution, preferably 0.05%-1% citric acid aqueous solution. The ratio of the acidic solution and concentrated mixture by volume is between about 0.1:1 and about 20:1, for example. The two phases (aqueous and organic) are mixed thoroughly and were allowed to stand to separate. The bottom layer, i.e., water layer, is removed. The remained top layer is washed 1-20 times using the same method, i.e. addition of acidic solution while being stirred and mixed, separation of two layers and removal of the bottom water layer. The ratio of the acidic solution and concentrate by volume is about 0.1:1 to about 10:1, for example. After washing, the organic phase and aqueous phase are collected, respectively. The aqueous phase is concentrated and dried to form the product. The organic phase is further processed.

Pure water is added to the organic solution obtained. The ratio of pure water and ester organic phase solution is between about 1:1 and about 1:50 by weight, for example. This is concentrated at controlled temperature, preferably at or below 80° C.

Filtration: the concentrate solution obtained from step G is cooled to 10° C.-60° C., for example, then filtered. The filtrate is collected.

Concentration and Drying: Filtrate obtained from step (h) is further concentrated to the solid content of 15%-80%. The resulting concentrate is dried by lyophilization, or spray drying, ground, and screened to obtain product theaflavins.

Preferred features of the process described herein include temperatures of the concentration/lyophilization is controlled at −35° C. or below, the vacuum level is about 0.6-1 mmHg. The water vapor is evaporated from the ice block particles of theaflavins concentrate, then, the temperature is increased at the rate of 1-5° C./hour to 0° C., then the temperature is increased at the rate of 1-10° C. to 25° C.-30° C., keeping for 1-4 ho example, until the water content of the product reaches to 3%-5%, and finally, the vacuum is released.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating or preventing a disease, is sufficient to effect such treatment or prevention of the disease. The "therapeutically effective amount" will vary depending on the disease and its severity and the age, weight, etc., of the patient to be treated.

Further, in certain embodiments, compounds of the invention and/or pharmaceutical compositions thereof are administered to a patient, preferably a human, as a preventative measure against the above diseases or conditions. Thus, the theaflavins of the invention and/or compositions thereof may be administered as a preventative measure to a patient having a predisposition for any of the above diseases or disorders. Accordingly, the theaflavins of the invention and/or pharmaceutical compositions thereof may be used for the treating or preventing one disease or disorder and concurrently treating or preventing another (e.g., preventing hyperlipidemia while treating a cerebral infarction).

The suitability of the theaflavins of the invention and/or compositions thereof in treating or preventing the various diseases or disorders listed above may be determined by methods described in the art. Accordingly, it is well within the capability of those of skill in the art to assay and use the compounds of the invention and/or pharmaceutical compositions thereof to treat or prevent the above diseases or disorders.

Therapeutic/Prophylactic Administration

The theaflavins of the invention and/or compositions thereof may be advantageously used in human and veterinary medicine.

When used to treat or prevent the above diseases or disorders, theaflavins of the invention and/or compositions thereof may be administered or applied singly, or in combination with other agents. The compounds of the invention and/or pharmaceutical compositions thereof may also be administered or applied singly, in combination with other pharmaceutically active agents including other compounds of the invention and/or pharmaceutical compositions thereof.

The current invention provides methods of treatment and prophylaxis by administration to a patient of a therapeutically effective amount of a compound of the invention and/or pharmaceutical composition thereof. The patient is preferably a mammal and most preferably, is a human.

The compounds of the invention and/or pharmaceutical compositions thereof are preferably administered orally, which results in the release of the compounds of the invention and/or pharmaceutical compositions thereof into the bloodstream. The compounds of the invention and/or pharmaceutical compositions thereof can be delivered via oral sustained release systems. In one embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, Int. J. Pharm. Tech. & Prod. Mfr. 1984, 5(3) 1-9). Factors affecting drug release are well known to the skilled artisan and have been described in the art (Bamba et al., Int. J. Pharm. 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In still another embodiment, OROS™ osmotic devices are used for oral sustained release delivery devices (Theeuwes et al., U.S. Pat. No. 3,845,770; Theeuwes et al., U.S. Pat. No. 3,916,899).

In one embodiment, the compounds of the invention are encapsulated for oral administration. Preferably, encapsulation protects the compounds of the invention from light and/or oxygen degradation. The capsule preferably, is comprised of a shell and a fill material, where either the shell or fill material contains an radiation blocker and/or an anti-oxidant.

The shell material is comprised of a gelling agent, water and optionally a plasticizer. Accordingly, the shell material may form either a hard gel or a soft gel. The gelling agent may be, but is not limited to, gelatin, modified starch, carrageenan, gellan, mannan gum, amylose, xanthan, alginates, agar, guar, gum arabic, pectin, cyclodextrin or combination thereof The shell may optionally include an emulsifier, thickener, preservative, flavoring, sweetener, colorant, radiation blocker, opacifying agent, anti-oxidant, masticatory substance, etc.

Gelatin, as is well known in the art, is manufactured by the hydrolysis of animal by-products such as bones, skin, and connective tissue which contain collagen. Bovine animals and pigs are the primary sources of gelatin Modified starches, include, for example, non-retrograding starches derived by chemical modification of starch from any plant source such as corn, waxy maize, potato, wheat, rice, tapioca, sorghum, etc. Useful modified starches are ether and ester derivatives of starch including, for example, hydroxypropyl, hydroxyethyl, succinate, and octenyl succinate starch derivatives. Other modified starches which may be used include the thermally converted, fluidity or thin boiling type products derived from the above chemically modified starches. These materials may be of lower molecular weight, prepared by heating the modified starch, subjecting the starch to hydrolytic acid and/or heat treatment, etc.

Carrageenan is a natural sulfated polysaccharide hydrocolloid derived from seaweed, and is a mixture of galactose and 3-6-anhydrogalactose copolymers. A number of different carrageenan types exist (e.g., kappa, iota, lambda, etc.) and it is anticipated that any of these may be used in the present invention.

Gellan gum is an extracellular polysaccharide obtained by aerobic fermentation of the microorganism, *Pseudomonas elodea*. Various forms of gellum gum including, but not limited to, native, deacetylated, deacylated clarified, partially deacetylated, partially deacylated clarified may be sued in the present invention.

Mannam gum include the galactomannan gums, the glucomannan gums and mixtures thereof. Accordingly, mannam gum includes, but is not limited to, locust bean gum, konjac gum, tara gum and cassia gum.

In some embodiments, a gelling salt may be used in the present invention. Accordingly, a calcium salt, a magnesium salt, a barium salt, a sodium salt or a potassium salt of an appropriate inorganic or organic acid may be used to form the shell of a capsule of the present invention.

Plasticizers are preferably, polyols, such as, for example, glycerin, sorbitol, an alkylene glycol, maltitol, lactitol, xylitol, corn syrup solids, etc. and combinations thereof. In one embodiment, the plasticizer is a combination of glycerin and sorbitol.

In another embodiment, the capsule shell comprises between about 10% and 90% gelatin, and between about 5% and about 40% water. In another embodiment, the capsule shell comprises between about 10% and 90% gelatin, between about 1% and about 30% plasticizer and between about 5% and about 40% water. In still another embodiment, the capsule shell comprises between about 25 to about 45% gelatin, between about 1% and about 30% plasticizer and between about 5% and about 40% water. In still another embodiment, the capsule shell comprises between about 25 to about 45% gelatin, between about 1% and about 30% plasticizer, between about 1 and 5% radiation blocker and between about 1% and about 5% colorant and between about 5% and about 40% water.

The capsule shell of the present invention encloses a preselected quantity of fill material. Preferably, the enclosed fill material will contain a therapeutically effective amount of a mixture of theaflavins. The fill material may be a liquid, a semi-solid, a solid and gel.

The fill material may include a pharmaceutically acceptable vehicle, which may be prepared by a number of diverse methods which are known to those of skill in the art. The pharmaceutically acceptable vehicle must be compatible with the capsule shell and preferably, does not degrade the capsule shell during a period of typical storage. Solutions to the above problem are well known to the skilled artisan.

Suitable liquid pharmaceutically acceptable vehicles for the fill material include, but are not limited to, neutral oil, mineral oil, water, alcohol, polyalkylene glycol, vegetable oil and fructose syrup. Preferably, the liquid pharmaceutically acceptable vehicle is a vegetable oil, more preferably, a corn oil, peanut oil, safflower oil, sunflower oil and soybean oil and most preferably soybean oil. The liquid pharmaceutically acceptable vehicle may include an emulsifier, thickener, preservative, flavoring, sweetener, colorant, radiation blocker, opacifying agent, anti-oxidant, masticatory substance, etc.

The present capsules may also include a solid fill material. Useful solid fill materials include, but are not limited to, tablets or pellets comprising the mixture of theaflavins, which may be further coated with gelatin, sugar, etc. (Glassman, U.S. Pat. No. 3,228,789). The tablets or pellets may contain co-solvents, buffers, emulsifiers, thickeners, preservatives, sweeteners, flavorings, colorants, radiation blockers, anti-oxidants, opacifying agent, masticatory substances, etc.

The present capsules may also include a semi-solid fill material. The mixture of theaflavins may, for example, be dispersed in a substantially water-free carrier mixture comprising one or more polyalkylene glycols, preferably, comprising a mixture of liquid polyalkylene glycol and waxy polyalkylene glycol and in minor amount a $C2-C_4$ diol or triol (Shah et al., U.S. Pat. No. 4,935,243). A flavoring, preservative, sweetener, colorant, radiation blocker, co-solvent, buffer, emulsifier, thickener, anti-oxidant, opacifying agent, masticatory substance, etc., may be added to the semi-solid fill material.

The present capsules may also enclose a gel fill comprising a gelled polymeric matrix, which may be generated by gelling a liquid fill followed by encapsulation (Cohen et al, U.S. Pat. No. 4,708,834). The gelled fill may comprise a solution or dispersion of an active ingredient in a polysaccharide gum and may also optionally, include co-solvents, preservative, buffers, emulsifiers, thickeners, sweeteners, flavorings, colorant, radiation blocker, opacifying agent, anti-oxidant, masticatory substance, etc.

Masticatory substances, for example, include, but are not limited to, Chicle, Chiquibul, Crown gum, Gutta hang kang, Massaranduba balata, Massaranduba chocolate, Nispero, Leche caspi, Pendare, Perillo, Leche de vac, Niger gutta, Tunu, Chite and Natural rubber. Flavorings include, but are not limited to, cherry syrup, citric acid, dextrose, essential oil, vanillin, cinnamon oil, orange oil, spearmint oil, strawberry oil, nutmeg oil. A preferred stiffener is beeswax while a preferred emulsifier is lecithin. Other stiffeners and emulsifiers which may be useful in the present invention are known to the skilled artisan. Preferred anti-oxidants include ascorbic acid and vitamin E.

In one embodiment, the fill material comprises between about 1% and about 20% mixture of theaflavins, between about 1% and about 5% anti-oxidant, between about 5% and about 90% pharmaceutically acceptable carrier, between about 1% and about 20% emulsifier; and between about 1% to about 20% stiffening agent.

Oral Dosage Compositions

The present oral dosage compositions typically contain a therapeutically effective amount of a compound of the invention, preferably in purified form, together with a suitable amount of a pharmaceutically acceptable vehicle, so as to provide the form for proper administration to a patient. The compounds of the invention may be present at a level of between about 5% and about 50% (w/w), preferably, about 11% in a pharmaceutical composition, for example. Total amount of the compound of the invention per dose may be between about 70 mg and about 210 mg.

When administered to a patient, the compounds of the invention and pharmaceutically acceptable vehicle are preferably sterile. Water, saline solutions and aqueous dextrose and glycerol solutions may be employed as liquid vehicles. Other suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents or pH buffering agents. In addition, auxiliary, stabilizing, thickening, lubricating and coloring agents may be used. A general discussion of the preparation of pharmaceutical compositions may be found in Remington, "The Science and Practice of Pharmacy," 19th Edition.

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations which can be used pharmaceutically.

The present pharmaceutical compositions can take the form of solutions, suspensions, emulsion, tablets, pills, pellets, capsules, capsules containing liquids, powders, sustained-release formulations, emulsions or any other form suitable for oral use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington, "The Science and Practice of Pharmacy," 19th Edition, 1995). Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, when in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM), etc. Additionally, flavoring agents, preservatives, coloring agents, bile salts, acylcamitines and the like may be added. For buccal administration, the pharmaceutical compositions may take the form of tablets, lozenges, etc. formulated in conventional manner.

When a compound of the invention is acidic or basic, it may be included in any of the above-described formulations as the free acid or free base, a pharmaceutically acceptable salt, a solvate or hydrate. Pharmaceutically acceptable salts substantially retain the activity of the free acid or base, may be prepared by reaction with bases or acids and tend to be more soluble in aqueous and other protic solvents than the corresponding free acid or base form.

Therapeutic Doses

Theaflavins of the invention and/or pharmaceutical composition thereof, will generally be used in an amount effective to achieve the intended purpose. For use to treat or prevent diseases or disorders the compounds of the invention and/or pharmaceutical compositions thereof, are administered or applied in a therapeutically effective amount.

The amount of a compound of the invention and/or pharmaceutical composition thereof that will be effective in the treatment of a particular disorder or condition disclosed herein will depend on the nature of the disorder or condition, and can be determined by standard clinical techniques known in the art and by doctors skilled in treating or preventing a particular disease or disorder. In addition, in vitro or in vivo assays may optionally be employed to help identify optimal dosage ranges. The amount of a compound of the invention and/or pharmaceutical composition thereof administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In one embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration are dependent on the nature of the compounds of the invention administered (e.g., whether the theaflavins are administered together or whether theaflavin, theaflavin-3-gallate, theaflavin-3'-gallate or theaflavin-3,3'-digallate are administered, each as a separate compound) but are generally about 0.001 mg to about 200 mg of a compound of the invention per kilogram body weight. In one embodiment, the dosage range is between about 0.1 mg/kg to about 5 mg/kg. Dosage ranges may be readily determined by methods known to the artisan of ordinary skill. Effective doses may be extrapolated from dose-response curves derived from in vitro or animal model test systems. Such animal models and systems are well-known in the art.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred. The compounds of the invention may also be demonstrated to be effective and safe using animal model systems.

Preferably, a therapeutically effective dose of a compound of the invention and/or pharmaceutical composition thereof described herein will provide therapeutic benefit without causing substantial toxicity. Toxicity of compounds of the invention and/or pharmaceutical compositions thereof may be determined using standard pharmaceutical procedures and may be readily ascertained by the skilled artisan. The dose ratio between toxic and therapeutic effect is the therapeutic index. A compound of the invention and/or pharmaceutical composition thereof will preferably exhibit particularly high therapeutic indices in treating disease and disorders. The dosage of a compound of the invention and/or pharmaceutical composition thereof described herein will preferably be within a range of circulating concentrations that include an effective dose with little or no toxicity.

Combination Therapy

In certain embodiments of the present invention, the compounds of the invention and/or pharmaceutical compositions thereof can be used in combination therapy with at least one other therapeutic agent. The compound of the invention and/or pharmaceutical composition thereof and the therapeutic agent can act additively or, more preferably, synergistically. In a preferred embodiment, a compound of the invention and/or a pharmaceutical composition thereof is administered concurrently with the administration of another therapeutic agent. In another embodiment, a compound of the invention and/or pharmaceutical composition thereof is administered prior or subsequent to administration of another therapeutic agent.

In particular, in one preferred embodiment, the compounds of the invention and/or pharmaceutical compositions thereof can be used in combination therapy with other agents used to treat or prevent hyperlipidemia, coronary heart disease, apoplexy, arthesclerotic cardiovascular diseases, AIDS, diabetes, oxidated-low density lipoprotein level, von Willebrand's disease, leukopenia, cerebral infarction, dementia and physical disorder and fatty liver.

Diet Supplement Compositions

The present diet supplement compositions typically contain one or more compounds of the invention, preferably in purified form, together with a suitable amount of a diet supplement vehicle, so as to provide the form for proper administration to a user.

There are many types of nutrition bars and other "snack" bars available on the market, and many consumers use such products as a convenient food source. For example, grain based bars such as granola bars are easy to carry and provide a healthy, good tasting food that is consumed by active people such as hikers and athletes, and by everybody else. Because grain-based nutrition bars are convenient and healthy, they have become a very popular product.

One type of bar that has become popular in the recent years is commonly called an "energy bar" or "performance bar." U.S. Pat. No. 7,247,336, for example is herein incorporated by reference. U.S. Pat. No. 6,143,335, McKenzie, R. G., for example, teaches scoring a food bar into bite-sized pieces thus providing a method for delivering exact quantities of supplemental ingredients to animals or humans. These products are typically especially formulated for use by active individuals such as athletes, and include ingredients that are intended to boost athletic performance, endurance, etc. Such energy bars provide an easy way for athletes to consume foods that are especially formulated to improve performance.

EXAMPLES

Example I

Figure 1:
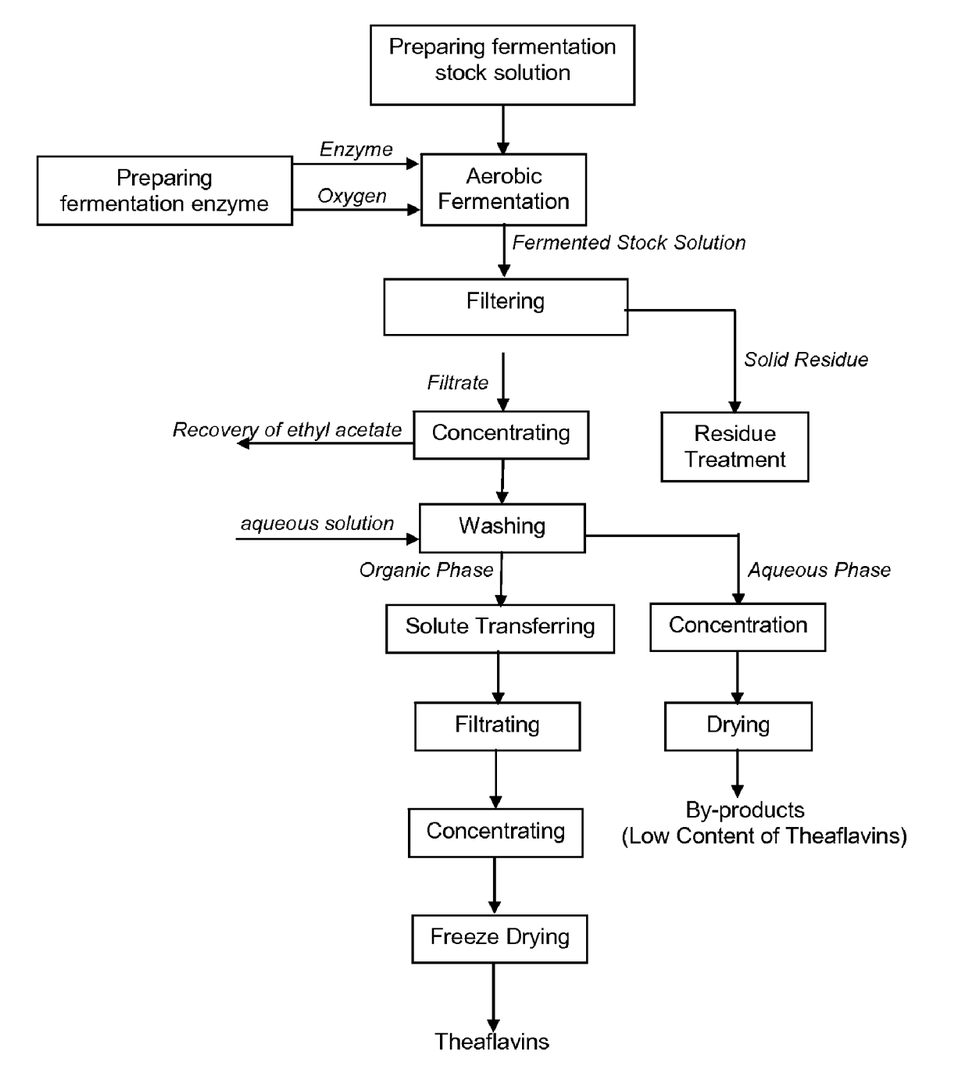
FIG. 1 displays a process embodiment of the present invention for manufacturing theaflavins.

See, FIG. 1. (1) To an example extraction container (2000 ml electric stirring device, flask with three-neck, condensing tube and water bath.), 100 g of green tea was added, followed by the addition of 1000 ml ethyl acetate. The temperature was controlled at a range of 25° C.-60° C. Thus formed mixture was stirred at speed of 30-150 rpm for 30 min. The liquid layer (or extraction solution) was then collected. To the solid residue, another 1000 ml of ethyl acetate was added. The extraction process was repeated. The extracted solution was combined and concentrated at vacuum −0.085 Mpa and 70° C. in a rotating evaporator (Model: RE-200, Manufacturer: Shanghai Kexing Instrument Co.), to a suspension that contains approximate 1% (w/v) of the solid. The suspension was then cooled to ambient temperature and thus formed the fermentation stock solution. (2) The starting enzyme was prepared from 120 g of fresh tea leaves. The fresh tea leaves were sprinkled with pure water or a 0.05-1% citric acid aqueous solution, then cooled to 0° C. or below and frozen for a minimum of 2 hours. The frozen tea leaves were crushed to small particles of about 80 mesh at a room temperature. Thus prepared enzyme materials were ready to use (storing time is less than 2 hours at ambient temperature). (3) To a fermentation container (glass reactor, Model: DAT serial, Manufacturer: Shanghai Kexing Instrument Co.), 1000 g of fermentation stock solution prepared from step (1) and 100 g of enzyme materials prepared in step (2) were added and oxygen was introduced at flow rate of 600 ml/min, while the mixture was stirred at 30-150 rpm at 20-60° C. Analytical samples were collected from the fermentation container at each 30 min for a total time of 4-8 hours depending on the actual analytical results. When the reaction was complete, both oxygen flow and stirring were stopped. The end point of the reaction is determined by a curve of time-absorption value prepared at 380 nm, e.g. when the absorption value for theaflavins is steady as time increases, the end point is considered to be reached. (4) Immediately after the reaction was stopped, the reaction mixture was filtered through a 120 mesh filter screen. Both the filtrate and the solid residue were collected. The solid residue was treated and then dried as a byproduct. The filtrate was concentrated at temperature of 60-80° C. and vacuum of −0.085 Mpa or above, by using rotating evaporator (Model: RE-200, Manufacturer: Shanghai Kexing Instrument Co.). When the solid content in the solution reached 8% (w/v), the concentrated solution was transferred to a washing container (Pear Shape Separatory Funnel, 500 ml, Manufacturer: Shanghai Shendi Glassware Co.). The concentrated solution (ethyl acetate solution) was washed with 0.05% citric acid aqueous solution. The volume of washing solution is equal to 20% of the concentrated solution, and the ethyl acetate solution was washed 8 times. Both the organic layer and the aqueous layer were collected. The combined aqueous layer was concentrated and dried to yield byproducts. To the organic layer (ethyl acetate layer), 100 ml water was added and the resulted mixture was further concentrated at 60-80° C. till the substantially complete removal of ethyl acetate. The aqueous layer (theaflavins solution) was then collected and cooled to 40° C. The solution was filtered through a 120 mesh filter screen to remove insoluble impurities. The filtrate was collected and concentrated at about 60-80° C. and vacuum of −0.085 Mpa or above to solid content of 40% (w/v). The concentrator used in above steps is a rotating evaporator (Model: RE-200, Manufacturer: shanghai Kexing Instrument Co., Ltd.). The resulted mixture was cooled to −35° C., then lyophilized under a vacuum of 0.6-1 mmHg. Upon the removal of the ice chunk or ice particles and under the same vacuum condition, the temperature of the solid product was increased gradually to 0° C. at a controlled rate at 3° C./hour, then to 25-30° C. at a controlled rate of 5° C./hour. After the solid product was dried under the same vacuum and 25-30° C. for 1-2 hours and the water content reached 3%-5% in the solid product, the vacuum was released and the solid product was crushed by a micro high speed mill (Model: XA-1, Particle Size: 80-150 mesh, Manufacturer: Jiangyan Yinhe Instrument Co., Ltd.) and screened through a screen grader to give 6.2 g of theaflavins product. Analysis of the product showed the theaflavins content of 46.2%. (w/w)

Example II

A process of manufacturing theaflavins: (1) As shown in Figure I, to an extraction container (2000 ml, specially designed and assembled by inventors, which is consisted of electric stirring device, flask with three-neck, condensing tube and water bath.), 100 g of green tea was added, followed by the addition of 1500 ml ethyl acetate. The temperature was controlled at a range of 20° C.-40° C. Thus formed mixture was stirred at speed of 30-150 rpm for 30 min. The organic phase (or extraction solution) was collected. To the solid residue, another 1500 ml of ethyl acetate was added and the above extraction process was repeated. The extracted organic phases were combined and concentrated at vacuum −0.085 Mpa and 70° C. in a rotating evaporator (Model: RE-200, Manufacturer: Shanghai Kexing Instrument Co., Ltd.) to a suspension that contains approximately 0.8% (w/v) of solid. The suspension was then cooled to ambient temperature and thus formed the fermentation stock solution. (2) The starting fermentation enzyme was prepared from 180 g of fresh tea leaves. The fresh tea leaves were sprinkled with pure water or a citric acid aqueous solution (0.5%), then cooled to 0° C. or below and frozen for a minimum of 2 hours. The frozen tea leaves were crashed to small particles of 80 mesh below room temperature. Thus prepared fermentation enzyme was ready to use (storing time is less than 2 hours at ambient temperature). (3) To a fermentation container (glass reactor, Model: DAT serial, Manufacturer: Shanghai Kexing Instrument Co., Ltd), 1500 g of fermentation stock solution prepared from step (1) and 150 g of fermentation enzyme materials prepared in step (2) were added and oxygen was introduced at flow rate of 600 ml/min while the mixture was stirred at 30-150 rpm at 20-25° C. Analytical samples were collected from the fermentation container every 30 min for a total time of 4-8 hours depending on the actual analytical results. Both oxygen flow and stirring were stopped, and thus the process was stopped completely. The end point of the reaction is determined by a curve of time-absorption value prepared at 380 nm, e.g. when the absorption value for theaflavins is steady as time increases, the end point is considered to be reached. (4) Immediately after the reaction was stopped, the reaction mixture was filtered through a 120 mesh filter screen. Both the filtrate and the solid residue were collected. The solid residue was treated and then dried as a byproduct. The filtrate was concentrated at temperature of 60-80° C. and vacuum of −0.085 Mpa or above, by using rotating evaporator (Model: RE-200, Manufacturer: Shanghai Kexing Instrument Co., Ltd.). When the solid content in the solution reached 8% (w/v), the concentrated solution was transferred to a washing container (Pear Shape Separatory Funnel, 500 ml, Manufacturer: Shanghai Shendi Glassware Co., Ltd.). The concentrated solution (ethyl acetate solution) was washed with 0.05% citric acid aqueous solution. The volume of washing solution is equal to 10% of the concentrated solution and the ethyl acetate solution was washed 8 times. Both the organic layer and the aqueous layer were collected. The combined aqueous layer was concentrated and dried to yield byproducts. To the organic layer (ethyl acetate layer), 140 ml of water was added and the resulting mixture was further concentrated at 80° C. or below till the complete removal of ethyl acetate. The aqueous layer (theaflavin solution) was then collected and cooled to 40° C. The solution was filtered through a 100 mesh filter screen to remove insoluble impurities. The filtrate was collected and concentrated at about 60-80° C. and vacuum of −0.085 Mpa or above to solid content of 40% (w/v). The concentrator used in above steps is a rotating evaporator (Model: RE-200, Manufacturer: shanghai Kexing Instrument Co., Ltd.). The resulted mixture was cooled to −35° C., then lyophilized under a vacuum of 0.6-1 mmHg. Upon the removal of the ice chunk or ice particles and under the same vacuum condition, the temperature of the solid product was increased gradually to 0° C. at a controlled rate at 3° C./hour, then to 25-30° C. at a controlled rate of 5° C./hour. After the solid product was dried under the same vacuum at 25-30° C. for 1-2 hours and the water content reached 3%-5% in the solid product, the vacuum was removed. The solid product was crashed by a micro high speed mill (Model: XA-1, Particle Size: 80-150 mesh, Manufacturer: Jiangyan Yinhe Instrument Co., Ltd.) and screened through a screen grader to give 6.4 g of theaflavin product. Analysis of the product showed a theaflavin content of 45.8% (w/w).

Example III

A process of manufacturing theaflavins: (1) As shown in Figure I, to an extraction container (5000 ml, specially designed and assembled by inventors, which is consisted of electric stirring device, flask with three-neck, condensing tube and water bath.), 100 g of green tea was added, followed by the addition of 3000 ml ethyl acetate. The temperature was controlled at a range of 25° C.-60° C. Thus formed mixture was stirred and extracted at speed of 30-150 rpm for 30 min. The organic phase (or extraction solution) was collected. To the solid residue, another 3000 ml of ethyl acetate was added and the above extraction process was repeated. The extracted organic phases were combined and concentrated at vacuum −0.085 Mpa and 70° C. in a rotating evaporator (Model: RE-200, Manufacturer: Shanghai Kexing Instrument Co., Ltd.), to a suspension that contains approximately 0.5% of solid (w/v). The suspension was then cooled to ambient temperature and thus formed the fermentation stock solution. (2) The fermentation enzyme was prepared from 180 g of fresh tea leaves. The fresh tea leaves were sprinkled with pure water or a citric acid aqueous solution (1%), then cooled to 0° C. or below and frozen for a minimum of 2 hours. The frozen tea leaves were crashed to small particle size of 80 mesh below room temperature. Thus prepared fermentation enzyme was ready to use (storing time is less than 2 hours at ambient temperature). (3) To a fermentation container (glass reactor, Model: DAT serial, Manufacturer: Shanghai Kexing Instrument Co., Ltd), 3000 g of fermentation stock solution prepared from step (1) and 150 g of enzyme materials prepared in step (2) were added and oxygen was introduced at flow rate of 600 ml/min, while the mixture was stirred at 30-150 rpm at 20° C. Analytical samples were collected from the fermentation container every hour till the fermentation process was essentially complete. The total period of time of fermentation is 4-8 hours depending on the actual test results. Both oxygen flow and stirring were stopped, and thus the process was stopped completely. The end point of the reaction is determined by a curve of time-absorption prepared at 380 nm, e.g. when the absorption value is steady as time increases, the end point is considered to be reached. (4) Immediately after the reaction was stopped, the reaction mixture was filtered through a 120 mesh filter screen. Both the filtrate and the solid residue were collected. The filtrate was concentrated at temperature of 60-80° C. and vacuum of −0.085 Mpa or above, by using rotating evaporator (Model: RE-200, Manufacturer: Shanghai Kexing Instrument Co., Ltd.). When the solid content in the solution reached 15% (w/v), the concentrated solution was transferred to a washing container (Pear Shape Separatory Funnel, 500 ml, Manufacturer: Shanghai Shendi Glassware Co., Ltd.). The concentrated solution (ethyl acetate solution) was washed with 1% citric acid aqueous solution. The ethyl acetate solution was washed 8 times. Both the organic layer and the aqueous layer were collected. The combined aqueous layer was concentrated and dried to yield byproducts. To the organic layer (ethyl acetate layer), 50 ml water was added and the resulted mixture was further concentrated at 80° C. till the complete removal of ethyl acetate. The aqueous layer (theaflavins solution) was then collected and cooled to 30° C. The solution was filtered through a 100 mesh filter screen to remove insoluble impurities. The filtrate was collected and concentrated at about 70° C. and vacuum of −0.085 Mpa or above in a rotating evaporator (Model: RE-200, Manufacturer: shanghai Kexing Instrument Co., Ltd.) to solid content of 25% (w/v). The resulted mixture was cooled to −35° C., then lyophilized under a vacuum of 0.6-1 mmHg. Upon the removal of the ice chunk or ice particles and under the same vacuum condition, the temperature of the solid product was increased gradually to 0° C. at a controlled rate at 3° C./hour, then to 25-30° C. at a controlled rate of 5° C./hour. After the solid product was dried under the same vacuum at 25-30° C. for 1-2 hours and the water content reached 3%-5% in the solid product, the vacuum was removed and the solid product was crashed by a micro high speed mill (Model: XA-1, Particle Size: 80-150 mesh, Manufacturer: Jiangyan Yinhe Instrument Co., Ltd.) and screened through a screen grader to give 6.3 g of theaflavins product. Analysis of the product showed a theaflavins content of 46.1% (w/w).

Example IV

A process of manufacturing theaflavins: (1) As shown in Figure I, to an extraction container (2000 ml, specially designed and assembled by inventors, which is consisted of electric stirring device, flask with three-neck, condensing tube and water bath.), 100 g of green tea was added, followed by the addition of 1000 ml ethyl acetate. The temperature was controlled at a range of 25-60° C. Thus formed mixture was stirred and extracted at speed of 100-150 rpm for 30 min. The liquid layer (or extraction solution) was collected. To the solid residue, another 1000 ml of ethyl acetate was added and the above extraction process was repeated. The extracted solution was combined and concentrated at 60-80° C. and vacuum of −0.085 Mpa or above in a rotating evaporator (Model: RE-200, Manufacturer: Shanghai Kexing Instrument Co., Ltd.), to a suspension that contains approximate 1% of solid (w/v). The suspension was then cooled to ambient temperature and thus formed the fermentation stock solution. (2) The fermentation enzyme was prepared from 220 g of fresh tea leaves. The fresh tea leaves were sprinkled with pure water or a citric acid aqueous solution (0.1%), then cooled to 0° C. or below and frozen for a minimum of 2 hours. The frozen tea leaves were crashed to small particle size of 80 mesh below room temperature. Thus prepared fermentation enzyme was ready to use (storing time is less than 2 hours at ambient temperature). (3) To a fermentation container (glass reactor, Model: DAT serial, Manufacturer: Shanghai Kexing Instrument Co., Ltd), 1000 g of fermentation stock solution prepared from step (1) and 200 g of fermentation enzyme prepared in step (2) was added and oxygen was introduced at flow rate of 600 ml/min, while the mixture was stirred at 30-150 rpm at 20° C. Analytical samples were collected from the fermentation container every hour till the fermentation process was essentially complete. The total period of time of fermentation is 4-8 hours depending on the actual analytical results. Both oxygen flow and stirring were stopped, and thus the process was stopped completely. The end point of the reaction is determined by a curve of time-absorption prepared at 380 nm, e.g. when the absorption value is steady as time increases, the end point is considered to be reached. (4) Immediately after the reaction was stopped, the reaction mixture was filtered through a filter screen. Both the filtrate and the solid residue were collected. The filtrate was concentrated at temperature of 60-80° C. and vacuum of −0.085 Mpa or above, by using rotating evaporator (Model: RE-200, Manufacturer: Shanghai Kexing Instrument Co., Ltd.). When the solid content in the solution reached 8% (w/v), the concentrated solution was transferred to a washing container (Pear Shape Separatory Funnel, 500 ml, Manufacturer: Shanghai Shendi Glassware Co., Ltd.). The concentrated solution (ethyl acetate solution) was washed with 0.1% citric acid aqueous solution. The volume of washing solution is equal to 20% of the concentrated solution, and the ethyl acetate solution was washed 8 times. Both the organic layer and the aqueous layer were collected. The combined aqueous layer was concentrated and dried to yield byproducts. To the organic layer (ethyl acetate layer), 100 ml water was added and the resulted mixture was further concentrated at 60-80° C. till the complete removal of ethyl acetate. The aqueous layer (theaflavins solution) was then collected and cooled to 60° C. The solution was filtered through a 100 mesh filter screen to remove insoluble impurities. The filtrate was collected and concentrated at about 70° C. and vacuum of −0.085 Mpa or above to solid content of 80% (w/v). The concentrator used in above steps is a rotating evaporator (Model: RE-200, Manufacturer: shanghai Kexing Instrument Co., Ltd.) The resulting mixture was cooled to −35° C., then lyophilized under a vacuum of 0.6-1 mmHg. Upon the removal of the ice chunk or ice particles and under the same vacuum condition, the temperature of the solid product was increased gradually to 0° C. at a controlled rate at 3° C./hour, then to 25-30° C. at a controlled rate of 5° C./hour. After the solid product was dried under the same vacuum at 25-30° C. for 1-2 hours and the water content reached 3%-5% in the solid product, the vacuum was removed and the solid product was crashed by a micro high speed mill (Model: XA-1, Particle Size: 80-150 mesh, Manufacturer: Jiangyan Yinhe Instrument Co., Ltd.) and screened through a screen grader to give 6.2 g of theaflavins product. Analysis of the product showed a theaflavins content of 47.8% (w/w).

Example V

A process of manufacturing theaflavins: (1) As shown in Figure I, to an extraction container (3000 ml, specially designed and assembled by inventors, which is consisted of electric stirring device, flask with three-neck, condensing tube and water bath.), 200 g of green tea was added, followed by the addition of 2000 ml ethyl acetate. The temperature was controlled at a range of 25° C.-60° C. Thus formed mixture was stirred and extracted at speed of 30-150 rpm for 30 min. The liquid layer (or extraction solution) was collected. To the solid residue, another 2000 ml of ethyl acetate was added and the above extraction process was repeated once. The extracted solution was combined and concentrated at vacuum −0.085 Mpa and 70° C. in a rotating evaporator (Model: RE-200, Manufacturer: Shanghai Kexing Instrument Co., Ltd.), to a suspension that contains approximate 1% of solid (w/v). The suspension was then cooled to ambient temperature and thus formed the fermentation stock solution. (2) The fermentation enzyme was prepared from 220 g of fresh tea leaves. The fresh tea leaves were sprinkled with pure water or a citric acid aqueous solution (0.1%), then cooled to 0° C. or below and frozen for a minimum of 2 hours. The frozen tea leaves were crashed to small particle size of 80 mesh below room temperature. Thus prepared fermentation enzyme was ready to use (storing time is less than 2 hours at ambient temperature). (3) To a fermentation container (glass reactor, Model: DAT serial, Manufacturer: Shanghai Kexing Instrument Co., Ltd), 2000 g of fermentation stock solution prepared from step (1) and 200 g of fermentation enzyme prepared in step (2) was added and oxygen was introduced at flow rate of 600 ml/min, while the mixture was stirred at 30-150 rpm at 25° C. Analytical samples were collected from the fermentation container every hour till the fermentation process was essentially complete. Both oxygen flow and stirring were stopped, and thus the process was stopped completely. The total period of time of fermentation is 4-8 hours depending on the actual test results. The end point of the reaction is determined by a curve of time-absorption prepared at 380 nm, e.g. when the absorption value is steady as time increases, the end point is considered to be reached. (4) Immediately after the reaction was stopped, the reaction mixture was filtered through a 120 mesh filter screen. Both the filtrate and the solid residue were collected. The filtrate was concentrated at temperature of 60-80° C. and vacuum of −0.085 Mpa or above, by using rotating evaporator (Model: RE-200, Manufacturer: Shanghai Kexing Instrument Co., Ltd.). When the solid content in the solution reached 8% (w/v), the concentrated solution was transferred to a washing container (Pear Shape Separatory Funnel, 500 ml, Manufacturer: Shanghai Shendi Glassware Co., Ltd.). The concentrated solution (ethyl acetate solution) was washed with 0.1% citric acid aqueous solution. The volume of washing solution is equal to 20% of the concentrated solution, and the ethyl acetate solution was washed 20 times. Both the organic layer and the aqueous layer were collected. The combined aqueous layer was concentrated to yield byproducts. To the organic layer (ethyl acetate layer), 100 ml water was added and the resulted mixture was further concentrated at 60-80° C. till the complete removal of ethyl acetate. The aqueous layer (theaflavins solution) was then collected and cooled to 40° C. The solution was filtered through a 100 mesh filter screen to remove insoluble impurities. The filtrate was collected and concentrated at about 60-80° C. and vacuum of −0.085 Mpa or above in a rotating evaporator (Model: RE-200, Manufacturer: shanghai Kexing Instrument Co., Ltd.) to solid content of 40% (w/v). The resulted mixture was cooled to −35° C., and then lyophilized under a vacuum of 0.6-1 mmHg. Upon the removal of the ice chunk or ice particles and under the same vacuum condition, the temperature of the solid product was increased gradually to 0° C. at a controlled rate at 3° C./hour, then to 25-30° C. at a controlled rate of 5° C./hour. After the solid product was dried under the same vacuum and 25-30° C. for 1-2 hours and the water content reached 3%-5% in the solid product, the vacuum was removed and the solid product was crashed by a micro high speed mill (Model: XA-1, Particle Size: 80-150 mesh, Manufacturer: Jiangyan Yinhe Instrument Co., Ltd.) and screened through a screen grader to give 13.12 g of theaflavin product. Analysis of the product showed a theaflavins content of 47% (w/w).

Example VI

A process of manufacturing theaflavins: (1) As shown in Figure I, to an extraction container (2000 ml, specially designed and assembled by inventors, which is consisted of electric stirring device, flask with three-neck, condensing tube and water bath.), 100 g of green tea was added, followed by the addition of 1000 ml ethyl acetate. The temperature was controlled at a range of 25-60° C. Thus formed mixture was stirred and extracted at speed of 30-150 rpm for 30 min. The liquid layer (or extraction solution) was collected. To the solid residue, another 1000 ml of ethyl acetate was added and the above extraction process was repeated once. The extracted solution was combined and concentrated at vacuum −0.085 Mpa or at 70° C. in a rotating evaporator (Model: RE-200, Manufacturer: Shanghai Kexing Instrument Co., Ltd.), to a suspension that contains approximate 1% of solid (w/v). The suspension was then cooled to ambient temperature and thus formed a fermentation stock solution. (2) The fermentation enzyme was prepared from 220 g of fresh tea leaves. The fresh tea leaves were sprinkled with pure water or a citric acid aqueous solution (0.1%), then cooled to 0° C. or below and frozen for a minimum of 2 hours. The frozen tea leaves were crashed to small particle size of 80 mesh below room temperature. Thus prepared fermentation enzyme was ready to use (storing time is not more than 2 hours at ambient temperature). (3) To a fermentation container (glass reactor, Model: DAT serial, Manufacturer: Shanghai Kexing Instrument Co., Ltd), 1000 g of fermentation stock solution prepared from step (1) and 200 g of fermentation enzyme prepared in step (2) was added and oxygen was introduced at flow rate of 600 ml/min, while the mixture was stirred at 30-150 rpm at 25° C. Analytical samples were collected from the fermentation container every hour till the fermentation process was essentially complete. Both oxygen flow and stirring were stopped, and thus the process was stopped completely. The total period of time of fermentation is 4-8 hours depending on the actual test results. The end point of the reaction is determined by a curve of time-absorption prepared at 380 nm, e.g. when the absorption value is steady as time increases, the reaction is considered to be completed. (4) Immediately after the reaction was stopped, the reaction mixture was filtered through a 120 mesh filter screen. Both the filtrate and the solid residue were collected. The filtrate was concentrated at temperature of 60-80° C. and vacuum of −0.085 Mpa or above, by using rotating evaporator (Model: RE-200, Manufacturer: Shanghai Kexing Instrument Co., Ltd.). When the solid content in the solution reached 8% (w/v), the concentrated solution was transferred to a washing container (Pear Shape Separatory Funnel, 500 ml, Manufacturer: Shanghai Shendi Glassware Co., Ltd.). The concentrated solution (ethyl acetate solution) was washed with 0.1% citric acid aqueous solution. The volume of washing solution is equal to 20% of the concentrated solution and the ethyl acetate solution was washed once. Both the organic layer and the aqueous layer were collected. The combined aqueous layer was concentrated and dried to yield byproducts. To the organic layer (ethyl acetate layer), 100 ml water was added and the resulted mixture was further concentrated at 60-80° C. till the complete removal of ethyl acetate. The aqueous layer (theaflavins solution) was then collected and cooled to 60° C. The solution was filtered through a 100 mesh filter screen to remove insoluble impurities. The filtrate was collected and concentrated at about 70° C. and vacuum of −0.085 Mpa or above in a rotating evaporator (Model: RE-200, Manufacturer: shanghai Kexing Instrument Co., Ltd.) to solid content of 50% (w/v). The resulted mixture was cooled to −35° C., then lyophilized under a vacuum of 0.6-1 mmHg. Upon the removal of the ice chunk or ice particles and under the same vacuum condition, the temperature of the solid product was increased gradually to 0° C. at a controlled rate at 3° C./hour, then to 25-30° C. at a controlled rate of 5° C./hour. After the solid product was dried under the same vacuum and 25-30° C. for 1-2 hours and the water content reached 3%-5% in the solid product, the vacuum was removed and the solid product was crashed by a micro high speed mill (Model: XA-1, Particle Size: 80-150 mesh, Manufacturer: Jiangyan Yinhe Instrument Co., Ltd.) and screened through a screen grader to give 6.1 g of theaflavins product. Analysis of the product showed a theaflavins content of 46% (w/w).

Example VII (1) To a extraction container (2000 ml, specially designed and assembled by inventors, which is consisted of electric stirring device, flask with three-neck, condensing tube and water bath.), 100 g of green tea was added, followed by the addition of 1000 ml ethyl acetate. The temperature was controlled at a range of 25° C.-60° C. Thus formed mixture was stirred at speed of 30-150 rpm for 30 min. The liquid layer (or extraction solution) was then collected. To the solid residue, another 1000 ml of ethyl acetate was added and the above extraction process was repeated. The extracted solution was combined and concentrated at vacuum −0.085 Mpa and 70° C. in a rotating evaporator (Model: RE-200, Manufacturer: Shanghai Kexing Instrument Co., Ltd.), to a suspension that contains approximate 1% (w/v) of the solid. The suspension was then cooled to ambient temperature and thus formed the fermentation stock solution. (2) The starting enzyme was prepared from 120 g of fresh tea leaves. The fresh tea leaves were sprinkled with pure water or a 0.1% citric acid aqueous solution, then cooled to 0° C. or below and frozen for a minimum of 2 hours. The frozen tea leaves were crushed to small particles of about 80 mesh at a room temperature. Thus prepared enzyme materials were ready to use (storing time is not more than 2 hours at ambient temperature). (3) To a fermentation container (glass reactor, Model: DAT serial, Manufacturer: Shanghai Kexing Instrument Co., Ltd), 1000 g of fermentation stock solution prepared from step (1) and 100 g of enzyme materials prepared in step (2) were added and oxygen was introduced at flow rate of 600 ml/min, while the mixture was stirred at 30-150 rpm at 20° C. Analytical samples were collected from the fermentation container at each 30 min for a total time of 4-8 hours depending on the actual analytical results. When the reaction was complete, both oxygen flow and stirring were stopped. The end point of the reaction is determined by a curve of time-absorption value prepared at 380 nm, e.g. when the absorption value for theaflavins is steady as time increases, the end point is considered to be reached. (4) Immediately after the reaction was stopped, the reaction mixture was filtered through a 120 mesh filter screen. Both the filtrate and the solid residue were collected. The solid residue was treated and then dried as a byproduct. The filtrate was concentrated at temperature of 60-80° C. and vacuum of −0.085 Mpa or above, by using rotating evaporator (Model: RE-200, Manufacturer: Shanghai Kexing Instrument Co., Ltd.). When the solid content in the solution reached 8% (w/v), the concentrated solution was transferred to a washing container (Pear Shape Separatory Funnel, 500 ml, Manufacturer: Shanghai Shendi Glassware Co., Ltd.). The concentrated solution (ethyl acetate solution) was washed with 0.1% citric acid aqueous solution. The volume of washing solution is equal to 20% of the concentrated solution, and the ethyl acetate solution was washed 8 times. Both the organic layer and the aqueous layer were collected. The combined aqueous layer was concentrated and dried to yield byproducts. To the organic layer (ethyl acetate layer), 100 ml water was added and the resulted mixture was further concentrated at 60-80° C. till the substantially complete removal of ethyl acetate. The aqueous layer (theaflavins solution) was then collected and cooled to 40° C. The solution was filtered through a 100 mesh filter screen to remove insoluble impurities. The solution was filtered through a 100 mesh filter screen to remove insoluble impurities. The filtrate was collected and concentrated at about 60-80° C. and vacuum of −0.085 Mpa or above to solid content of 20-60% (w/v). The concentrator used in above steps is a rotating evaporator (Model: RE-200, Manufacturer: shanghai Kexing Instrument Co., Ltd.) The concentrate was introduced to spray dryer (Model YC-015, Manufacturer: Wuxi Dongsheng Spray-granulating & Srying Equipment Plant) by pump. Inlet air temperature of the spray dryer was controlled at 180-220° C., when outlet air temperature reached at 80-100° C., collected the dried product, and then screened through a screen grader to give 6.6 g of theaflavins product. Analysis of the product showed the theaflavins content of 45.8%. (w/w).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described compositions and modes for carrying out the invention which are obvious to those skilled in the art or related fields are intended to be within the scope of the following claims.

What is claimed is:

1. A process for producing theaflavin extract comprising
providing a first batch of tea leaves;
combining an organic solvent selected from the group consisting of ester, alcohol, ketone, ether, or a combination thereof with the first batch of tea leaves;
extracting polyphenols from the first batch of tea leaves to produce an organic stock substrate solution of polyphenols in the organic solvent;
providing a second batch of tea leaves;
grinding the second batch of tea leaves to produce stock fermentation enzyme;
combining the organic stock substrate solution with the stock fermentation enzyme to produce a fermentation mixture;
fermenting the fermentation mixture in the organic solvent to produce theaflavins; and
separating the theaflavins from the fermentation mixture to produce theaflavin extract.

2. The process according to claim 1 wherein the first batch of tea leaves are green tea.

3. The process according to claim 1 wherein the ratio of the first batch of tea leaves to the organic solvent is between about 1:10 and about 1:30.

4. The process according to claim 3 wherein extracting polyphenols from the first batch of tea leaves proceeds for about 20 to about 60 minutes at between about 25° C. and about 60° C.

5. The process according to claim 4 wherein the organic stock substrate solution is concentrated by removing organic solvent to yield a solid content of about 0.5% to about 5% w/v.

6. The process according to claim 1 wherein the second batch of tea leaves are substantially frozen.

7. The process according to claim 1 wherein the fermentation mixture is a ratio of organic stock substrate solution to stock fermentation enzyme between about 5:1 to about 20:1 (w:w).

8. The process according to claim 7 wherein fermentation proceeds between about 4 and about 8 hours at a stirring speed between about 30 and about 150 rpm and at between about 20° C. and about 40° C.

9. The process according to claim 8 wherein oxygen is added to the fermentation mixture during fermentation.

10. The process according to claim 8, after fermentation, wherein a resulting organic phase is separated from the fermentation mixture.

11. The process according to claim 10 wherein water is added to the resulting organic phase in a ratio of between about 1:1 and about 1:25 by weight and substantially all organic solvent is removed to produce aqueous theaflavin extract.

12. The process according to claim 11 wherein insoluble impurities are separated from the aqueous theaflavin extract to produce aqueous theaflavin extract.

13. The process according to claim 12 wherein the aqueous theaflavin extract is lyophilized or spray dried.

14. The process according to claim 1 wherein the organic solvent is selected from the group consisting of methyl acetate, ethyl acetate, propyl acetate, and isopropyl acetate.

15. The process according to claim 1 wherein the organic solvent is selected from the group consisting of ethyl alcohol, propyl alcohol, and isopropyl alcohol.

16. The process according to claim 1 wherein the organic solvent is selected from the group consisting of butanone, diethyl ether, dipropyl ether, and methyl-tert-butyl ether.

17. The process according to claim 14 wherein the organic solvent is ethyl acetate.

\* \* \* \* \*